(12) United States Patent
Yan et al.

(10) Patent No.: US 8,747,913 B2
(45) Date of Patent: Jun. 10, 2014

(54) HERBAL EXTRACT PHARMACEUTICAL COMPOSITION AND METHOD FOR TREATING AND/OR PREVENTING OF HYPERLIPIDEMIA AND PROCESSES FOR PRODUCING THE SAME

(75) Inventors: Xijun Yan, Tianjin (CN); Boli Zhang, Tianjin (CN); Zhixin Guo, Tianjin (CN); Guoguang Zhu, Tianjin (CN); Zhengliang Ye, Tianjin (CN); Feng Wei, Tianjin (CN); Ruizhi Luo, Tianjin (CN)

(73) Assignee: Tasly Pharmaceutical Group Co., Ltd (CN)

( * ) Notice: Subject to any disclaimer, the term of this patent is extended or adjusted under 35 U.S.C. 154(b) by 1421 days.

(21) Appl. No.: 11/721,245

(22) PCT Filed: Dec. 5, 2005

(86) PCT No.: PCT/CN2005/002089
§ 371 (c)(1),
(2), (4) Date: Jun. 30, 2009

(87) PCT Pub. No.: WO2006/060951
PCT Pub. Date: Jun. 15, 2006

(65) Prior Publication Data
US 2009/0291154 A1 Nov. 26, 2009

(30) Foreign Application Priority Data
Dec. 10, 2004 (CN) .......................... 2004 1 0093887

(51) Int. Cl.
*A61K 36/00* (2006.01)
(52) U.S. Cl.
USPC ....................................... 424/725

(58) Field of Classification Search
USPC ........................................... 424/725
See application file for complete search history.

(56) References Cited

U.S. PATENT DOCUMENTS 5,958,417 A    9/1999   Hsu

FOREIGN PATENT DOCUMENTS

| CN | 1109353 | 10/1995 |
| CN | 1276219 | 12/2000 |
| CN | 1276219 A | * 12/2000 |
| CN | 129397 | 5/2001 |
| CN | 1383888 | 12/2002 |
| JP | 58172320 | 10/1983 |
| JP | 5268920 | 10/1993 |
| JP | 7048403 | 2/1995 |
| JP | 2002114696 | 4/2002 |
| WO | WO 01/13931 A1 | 3/2001 |

OTHER PUBLICATIONS

Flaws et al. 2002. The Treatment of Modern Western Medical Disease with Chinese Medicine. Blue Poppy Enterprises INC. p. 290.*
Zhu. Chinese Materia Medica. CRC Press. 1998. p. 393.*

(Continued)

*Primary Examiner* — Patricia Leith
(74) *Attorney, Agent, or Firm* — Evan Law Group LLC

(57) ABSTRACT

A pharmaceutical composition consisting of Radix Polygoni Multiflori extract, Salviae Miltiorrhizae extract, Fructus Crataegi extract and Radix Notoginseng extract is described, wherein the composition optionally contains a pharmaceutical carrier. Processes for producing the composition and methods for treating and/or preventing hyperlipidemia, treating and/or preventing fatty liver and lowering blood lipid level by administration of the pharmaceutical composition are also disclosed.

22 Claims, 6 Drawing Sheets

(56) References Cited

OTHER PUBLICATIONS

Ansel et al. Pharmaceutical Dosage Forms and Drug Delivery Systems. Lippincott Williams & Wilkins. 1999. pp. 180, 182, 184.*

Dupler. Retrieved from the internet. <http://findarticles.com/p/articles/mi_g2603/is_0005/ai_2603000555/>.Encyclopedia of Alternative Medicine / Apr. 6, 2001. pp. 1-3.*

The Herbal Encyclopedia. Retrieved from the internet on Dec. 4, 2011. Web archive date Feb. 20, 2003, <http://web.archive.org/web/20030210135948/http://www.naturalark.com/herbcomb.html>. 8 pages.*

Zhu. Chinese Materia Medica: Chemistry, Pharmacology, and Applications. CRC Press. 1998. pp. 393-394.*

Weil et al. The Best Alternative Medicine. Simon and Schuster. 2002. p. 123.*

Balch. Prescription for Herbal Healing: An Easy-to-Use A-Z Reference to Hundreds of Common Disorders and Their Herbal Remedies. Penguin. 2002. pp. 80-81.*

Bailey. Yoga Journal. Dec. 2002. No. 171. p. 38.*

Small et al. Canadian Medicinal Crops. NRC Research Press. 1999. p. 2.* webmd.com. Retrieved from the internet on Mar. 16, 2012. 2 pages. <http://www.webmd.com/cholesterol-management/how-high-cholesterol-leads-atherosclerosis>.* thefreedictionary.com. Retrieved from the internet on Mar. 16, 2012. pp. 1-6. <http://medical-dictionary.thefreedictionary.com/Hepatic+steatosis>.*

Song, S., et al., "Study on the effect of Polygonum multiflorum Thunb on the experimental hyperlipidemia", Journal of Hebei Traditional Chinese Medicine and Pharmacology, vol. 18, No. 4, pp. 90-91, (2003).

Zhang, M., et al., "Clinically therapeutic study of Dispel Fatty Decoction in combination with sodium alginate diester in 35 cases of fatty liver", Shaanxi Journal of Traditional Chinese Medicine, vol. 23, No. 10, pp. 903-904, (2002).

Li, X., et al, "Clinically therapeutic analysis of Liver-Softening and Fat-Reducing Capsule in 45 cases of fatty liver", Jiangsu Journal of Traditional Chinese Medicine, vol. 21, No. 6, pp. 15-16, (2000).

Yang, F., et al, "Clinical observation of Fat-Regulating and Liver-Strengthening Decoction in treatment of 60 cases of fatty liver", New Journal of Traditional Chinese Medicine, vol. 36, No. 3, pp. 39-40, (2004).

International Search Report for PCT/CN2005/002089, 6 pages, mailed Mar. 16, 2006.

European Search Report for European Patent Application No. 05817628.0 dated Apr. 16, 2009, 7 pages.

Cheng et al., "Preventive effect of traditional herbal formulae against experimental hypercholesterolemia in rats with special reference to blood lipoprotein cholesterol levels," Journal of Ethnopharmacology, 94, 275-278, 2004.

Li et al., "Protective effect of chitosan plus Polygonum multiflorum, *Salvia miltiorrhiza*, and *Achyronthes bidentata* on rats of experimental fatty liver," Abstract only, Database Biosis [online] Biosciences Information Service, 2 pages, 2002.

Zhao, Na et al., "Cardiotonic pills, a compound Chinese medicine, protects ischemia-reperfusion-induced microcirculatory disturbance and myocardial damage in rats", Am. J. Physiol. Heart Circ. Physiol, vol. 298, pp. H1166-H1176, (2010).

O'Brien, Kylie A. et al., "A Chinese herbal preparation containing radix *Salviae miltiorrhizae, Radix notoginseng* and *Borneolum syntheticum* reduces circulating adhesion molecules", Evidence-Based Complementary and Alternative Medicine, vol. 2011, Article ID 790784, pp. 1-6, (2011).

* cited by examiner

HERBAL EXTRACT PHARMACEUTICAL COMPOSITION AND METHOD FOR TREATING AND/OR PREVENTING OF HYPERLIPIDEMIA AND PROCESSES FOR PRODUCING THE SAME

FIELD OF THE INVENTION

The present invention relates to the pharmaceutical field. More specifically, the present invention relates to a pharmaceutical composition comprising *Polygonum multiflorum* Thunb, which provides the pharmacological effect of lowering blood lipid, their preparation method, their pharmacological effect and their use in preparation of the blood-lipid lowering drugs or the drugs for treatment and/or prevention of hyperlipidemia. The composition of the present invention and its corresponding preparations can be used for treatment and/or prevention of hyperlipidemia. Further, the present invention also relates to the method of utilizing the composition for treatment and/or prevention of hyperlipidemia.

BACKGROUND ARTS

*Polygonum multiflorum* Thunb (Tuber fleeceflower root), also named as the Shouwu and Chi Shouwu in Chinese, originated from the dried root tuber of a perennial voluble herb plant of Polygonaceae *Polygonum multiflorum* Thunb, which belongs to a wild plant. It abounds in a lot of regions of China, mainly including Henan Province, Hubei Province, Guangxi Province, Guangdong Province, Guizhou Province, Sichuan Province and Jiangsu Province, etc.

Modern pharmacological research showed that *Polygonum multiflorum* Thunb had diverse functions such as anti-aging, anti-fatigue, protecting liver and promoting rebirth and development of blood cells, etc. SONG, Shijun et al [SONG, Shijun et al, Study on the effect of *Polygonum multiflorum* Thunb on the experimental hyperlipidemia, Journal of Hebei Traditional Chinese Medicine and Pharmacology, 2003, Vol. 18, No. 4, 90-91] observed the effect of lowering blood lipid of *Polygonum multiflorum* Thunb on rats and mice, and explored its mechanism. As shown in the results, *Polygonum multiflorum* Thunb could markedly lower blood triglyceride and blood cholesterol in rats.

In addition to study on the single prescription, there are a lot of reports on the complex prescriptions comprising *Polygonum multiflorum* Thunb.

ZHANG et al. [ZHANG, Minfang et al, Clinically therapeutic study of Dispel Fatty Decoction in combination with sodium alginate diester in 35 cases of fatty liver, Shaanxi Journal of Traditional Chinese Medicine, 2002, Vol. 23, No. 10, 903-904] used the Dispel Fatty Decoction (*Salvia miltiorrhiza* Bunge, Fructus Crataegi, *Polygonum multiflorum* Thunb, Semen Cassiae, Radix Curcumae and Rhizoma atractylodis etc.) in combination with sodium alginate diester to treat 35 cases of fatty liver, and a control group of 23 cases was set up. The results showed a significant difference between the therapeutic group and the control group. It was indicated that the integration of traditional Chinese medicine (TCM) and western medicine for treatment of fatty liver possessed many beneficial efficacies such as promoting lipid metabolism in liver, adjusting liver function and strengthening organic metabolism.

LI et al. [LI, Xiating et al, Clinically therapeutic analysis of Liver-Softening and Fat-Reducing Capsule in 45 cases of fatty liver, Jiangsu Journal of Traditional Chinese Medicine, 2000, Vol. 21, No. 6, 15-16] disclosed the application of the Liver-Softening and Fat-Reducing Capsule (which was prepared from Radix et Rhizoma Rhei Preparata, Radix Paeoniae Rubra, *Salvia miltiorrhiza* Bunge, crude Fructus Crataegi (Hawthorn fruit), *Polygonum multiflorum* Thunb and Concha Ostreae etc. for treating fatty liver. By regular check of liver functions, blood lipid and the imaging change of liver, the result showed a significant difference ($P<0.05$) on the liver function and blood lipid between pre-treatment and post-treatment, a marked morphological change of liver with light abnormal reaction. It was indicated that the capsule can effectively improve liver functions and the level of blood lipid of fatty liver patients with the marked improvement in the images of liver.

YANG et al. [YANG, Futai et al, Clinical observation of Fat-Regulating and Liver-Strengthening Decoction in treatment of 60 cases of fatty liver, New Journal of Traditional Chinese Medicine, 2004, Vol. 36, No. 3, 39-40] compared the curative effect on fatty liver of the Fat-Regulating and Liver-Strengthening Decoction (Prescription: Fructus Crataegi, *Polygonum multiflorum* Thunb, *Salvia miltiorrhiza* Bunge, *Poria cocos* (Schw.) Wolf, Pericarpium Citri Reticulatae, *Alisma orientalis* (Sam.) Juzep., Endothelium Corneum Gigeriae Galli, Rhizoma Zedoariae Preparata, Rhizoma Pinelliae Preparata, Semen Cassiae, Rhizoma curcumae longae, Powder of Radix Notoginseng) with those of the control drugs, and its therapeutic effects were observed. The resulting difference was of great significance ($P<0.01$), indicating that Fat-Regulating and Liver-Strengthening Decoction could not only facilitate metabolism of lipid in liver, lowering and adjusting lipid, but also have a good efficacy in the treatment of fatty liver.

It can be seen that most of aforementioned complex preparations of *Polygonum multiflorum* Thunb are complex, and unfavorable for industrialization. At the same time, the researches mostly focus on the therapy for fatty liver. Studies of their therapeutic effects on cardio and cerebral vascular diseases have never been carried out.

According to the theory of the TCM, *Polygonum multiflorum* Thunb has many functions such as nourishing liver and kidney, benefiting essence and blood and relaxing bowels. Modern pharmacological studies show that many positive efficacies had been found for this herbal medicine, which was present not only in lowering cholesterol, decreasing cholesterol absorption through intestine and stopping its deposition in blood, relieving and alleviating the formation of arteriosclerosis, holding back the stagnation of lipids in blood or permeation into endarterium, but also improving the microcirculation and preventing the formation of thrombus. Meanwhile, *Salvia miltiorrhiza* Bunge and Radix Notoginseng are characterized in promoting blood circulation and removing blood stasis and improving microcirculation. By working with Fructus Crataegi, the purposes of improving the microcirculation and lowering blood lipid may be achieved simultaneously, and therefore will be beneficial to its therapeutic effects of hyperlipidemia in clinic.

On the basis of study on a large number of proved recipes, the inventor of the present invention put forward a new TCM composition that is simpler than those frequently-used, which has an excellent function of lowering blood lipid. Clinically, not only does it have evidently therapeutic effects on hyperlipidemia, but also on controlling and/or alleviating various cardio and cerebral vascular diseases.

DESCRIPTION OF THE INVENTION

The objective of the present invention is to provide a pharmaceutical composition comprising *Polygonum multiflorum* Thunb. Said composition and its preparations of all kind have a function of lowering blood lipid and can be used for treatment and/or prevention of hyperlipidemia and for controlling and/or alleviating various hyperlipidemia-related cardio and cerebral vascular diseases. This composition comprises *Polygonum multiflorum* Thunb, *Salvia miltiorrhiza* Bunge, Fructus Crataegi and Radix Notoginseng. The pharmaceutical composition may comprise the conventional pharmaceutically acceptable carriers.

All of the crude medicines used in this invention are in line with the standards of Chinese Pharmacopeia. They may be and preferably used as the form of the prepared medicinal herbs ("Yinpian" is referred to the herbs that are processed from the crude medicines).

The composition of the present invention can be prepared into any of conventional preparations, in particular oral preparations.

The composition of the present invention comprises 10 to 20 parts by weight of *Polygonum multiflorum* Thunb, 5 to 15 parts by weight of *Salvia miltiorrhiza* Bunge, 10 to 20 parts by weight of Fructus Crataegi and 1 to 10 parts by weight of Radix Notoginseng. Preferably, 15 parts by weight of *Polygonum multiflorum* Thunb, 10 parts by weight of *Salvia miltiorrhiza* Bunge, 15 parts by weight of Fructus Crataegi and 5 parts by weight of Radix Notoginseng.

The composition of the present invention may also comprise one or more pharmaceutically acceptable carriers, wherein said carriers may be the conventional ones known in the pharmaceutical area. For example, said carriers are liquid or solid excipients, diluters, wetting agents, preservatives, sweeteners, flavoring agents as well as colorants etc. In preparation of oral preparations, the most conventional carriers are exemplified as starch, lactose, talc powder and/or dextrine etc.

The type and/or amount of the carriers are selected according to the knowledge known in the pharmaceutical area. Generally, the amount of the carriers varies greatly, for example, the carriers may account for 1 wt % to even several folds of the total amount of the crude medicines.

Another objective of the present invention is to provide a method for preparing said pharmaceutical composition. Said composition can be prepared by a conventional method known in prior art. For example, the crude medicines of *Polygonum multiflorum* Thunb, *Salvia miltiorrhiza* Bunge, Fructus Crataegi and Radix Notoginseng are pulverized directly into powder, which is followed by preparing into the desired preparations.

More specifically, the method of the present invention comprises the following steps:
(1) Providing the crude medicines as follows: 10 to 20 parts by weight of *Polygonum multiflorum* Thunb, 5 to 15 parts by weight of *Salvia miltiorrhiza* Bunge, 10 to 20 parts by weight of Fructus Crataegi and 1 to 10 parts by weight of Radix Notoginseng;
(2) Pulverizing the aforesaid medicines into powder, blending; and
(3) Optionally adding the required pharmaceutical carrier(s) and preparing into desired preparations by a conventional method.

Alternatively, when preparing the composition of the present invention, *Polygonum multiflorum* Thunb, *Salvia miltiorrhiza* Bunge, Fructus Crataegi and Radix Notoginseng can be prepared into their extracts firstly, and then these extracts are prepared into the composition.

Specifically, the preparation method for the composition of the present invention comprises the following steps:
(1) Providing the crude medicines as follows: 10 to 20 parts by weight of *Polygonum multiflorum* Thunb, 5 to 15 parts by weight of *Salvia miltiorrhiza* Bunge, 10 to 20 parts by weight of Fructus Crataegi and 1 to 10 parts by weight of Radix Notoginseng;
(2) Pulverizing the aforesaid medicines into powder;
(3) Preparing extracts of *Polygonum multiflorum* Thunb, *Salvia miltiorrhiza* Bunge, Fructus Crataegi and Radix Notoginseng separately, blending all these extracts, or preparing the aforesaid extracts into powder, blending the powder of these extracts; and
(4) Optionally adding the required pharmaceutical carrier and preparing into desired preparations.

If needed, an additional drying step at temperature of about 50~60° C., for example 55° C., for about 10~12 hours may be further included in the method.

When preparing the extracts of *Polygonum multiflorum* Thunb, *Salvia miltiorrhiza* Bunge, Fructus Crataegi and Radix Notoginseng, each of four crude medicines can be extracted separately, or 2-4 kinds of these four crude medicines are mixed in random combination, such as the mixture of *Polygonum multiflorum* Thunb and *Salvia miltiorrhiza* Bunge, the mixture of *Salvia miltiorrhiza* Bunge and Radix Notoginseng, or the mixture of *Polygonum multiflorum* Thunb, *Salvia miltiorrhiza* Bunge and Radix Notoginseng, then the mixtures are extracted separately.

The aforesaid four crude medicines are extracted by conventional methods, for example, the methods are, but do not limited to, water extraction-alcohol precipitation method, percolate method, and column chromatography etc. For *Salvia miltiorrhiza* Bunge, the extract process may be selected from water extraction method, alcohol extraction method, or the method of water extraction-alcohol precipitation followed by separation with macro-porous resin; for *Polygonum multiflorum* Thunb, the extract process may be selected from water extraction method, or the method of alcohol extraction followed by separation with macro-porous resin; for Fructus Crataegi, the extract process may be selected from water extraction method, or the method of water extraction followed by separation with polyamide resin; for Radix Notoginseng, the extract process may be selected from ethanol extraction method, or the method of alcohol extraction followed by separation with macro-porous resin.

For conveniently understanding the invention, the extraction methods of the ingredients in the composition of the present invention are described below, which is not intended to limit the present invention.

Water extraction method of *Polygonum multiflorum* Thunb: *Polygonum multiflorum* Thunb was taken and pulverized, into which water was added and extracted for several times. The resulting extracts were combined and concentrated to give the *Polygonum multiflorum* Thunb extract.

Method of alcohol extraction followed by separation with macro-porous resin for *Polygonum multiflorum* Thunb: *Polygonum multiflorum* Thunb was taken and percolated with ethanol. The resulting percolate was applied on macro-porous resin column and washed with ethanol-water gradient system. The washing was collected and concentrated to give the *Polygonum multiflorum* Thunb extract.

Water extraction method of *Salvia miltiorrhiza* Bunge: *Salvia miltiorrhiza* Bunge was taken, pulverized and passed through 20-mesh sieve. Water was added to extract for two times. For the first time, the medicinal material was soaked in water (×9~10 folds) and extracted by heating for 1.5 hours, and for the second time, water (×5~7 folds) was added and extracted by heating for 1 hour. Resulting decoctions were combined, concentrated properly and added 95% ethanol to make the concentration of ethanol at 50~70%, then concentrated by recovering ethanol to give the *Salvia miltiorrhiza* Bunge extract.

Method of alcohol extraction of *Salvia miltiorrhiza* Bunge: *Salvia miltiorrhiza* Bunge was taken, pulverized and passed through 20-mesh sieve. The herb was extracted with 7~9-fold volume of 70% ethanol by heating reflux twice, one hour for each time. The extracts were combined and concentrated to give the *Salvia miltiorrhiza* Bunge extract.

The extraction method of the active fraction of *Salvia miltiorrhiza* Bunge (the method of water extraction-alcohol precipitation): the medicinal material of *Salvia miltiorrhiza* Bunge was taken, pulverized and passed through 20-mesh sieve and extracted with water or ethanol. The extract was concentrated and precipitated with ethanol. After recovering ethanol, the extract was dissolved with water and separated by macro-porous resin column. The column was washed with water to eliminate impurities, then to wash with ethanol until the active fraction was totally separated. The dried *Salvia miltiorrhiza* Bunge extract was obtained after recovering ethanol.

Water extraction method of Fructus Crataegi: Fructus Crataegi was taken and extracted with water at suitable temperature for several times, the extracts was combined and concentrated to obtain the Fructus Crataegi extract.

Method of alcohol extraction followed by separation with polyamide resin of Fructus Crataegi: Fructus Crataegi was taken, extracted with ethanol by refluxing for several times. The extracts were combined and concentrated properly, followed by being applied on polyamide resin column for further separation. The washing was collected and concentrated to give the Fructus Crataegi extract.

Method of alcohol extraction of Radix Notoginseng: Radix Notoginseng was extracted with 10-fold volume of 10%~30% ethanol for three times, refluxing by heating 8 hours. The extracts were combined and concentrated to recover ethanol to give the Radix Notoginseng extract.

The extraction method of the active fraction of Radix Notoginseng (the method of alcohol extraction-column chromatography): Radix Notoginseng was taken, pulverized properly and extracted with ethanol twice. After filtrated, the filtrate was combined and concentrated to certain volume by recovering ethanol under reduced pressure. A proper amount of water was added, followed by recovering ethanol until no smell of ethanol. The resulting extract was applied on pre-treated macro-porous resin column, washed with water until washing had no color and then washed with 50% ethanol. The eluents were collected and concentrated to give the Radix Notoginseng extract.

By means of two methods described above, the composition of the present invention can be obtained and further prepared into any of desired specified preparations, in particular oral preparations, for example either the oral solid ones such as tablet, pill, granule or capsule etc, or oral liquid preparations such as syrup and oral liquid. The composition can be added with conventional carriers by a conventional method known in the prior art to give a desired preparation.

For example, talc powder and dextrine may be used as the carriers in preparing of oral preparations with all kinds of crude medicine extracts. The total amount of talc powder and dextrine accounts for 7~20 wt % of the total amount of the crude medicine extracts, for example, the amount of talc powder accounts for 1~5 wt % and dextrine is 6~15 wt % of total amount of the crude medicine extracts. Preferably, talc powder is 1~2 wt % and dextrine is 6~7%.

Results of animal and clinical tests showed that the composition had the function of lowering blood lipid and can be used for treatment and/or prevention of hyperlipidemia.

Another objective of the present invention is to provide an application of the composition of the present invention in preparation of drugs for treatment of lowering blood lipid, as well as drugs for treatment and/or prevention of hyperlipidemia.

The pharmaceutical composition of the present invention may be used for treatment and/or prevention of hyperlipidemia, and for controlling and/or alleviating various hyperlipidemia-related cardio and cerebral vascular diseases.

Another objective of the present invention is to provide a method for treatment and/or prevention of hyperlipidemia, comprising administering a patient in need of this treatment with a therapeutically effective amount of the pharmaceutical composition and its corresponding preparations.

The compositions and their preparations produced by any one of method of the present invention may be used for lowering blood lipid or treating and/or preventing hyperlipidemia. In order to achieve this therapeutic purpose, daily orally-administrated amount of the composition for an adult patient corresponds to 10~50 g of the total amount of the crude medicine, preferably 20~30 g, once a day or several times such as two to three times. If they were used for prevention of disease, the dosage may be properly reduced.

BEST MODES OF THE INVENTION

Figure 1:
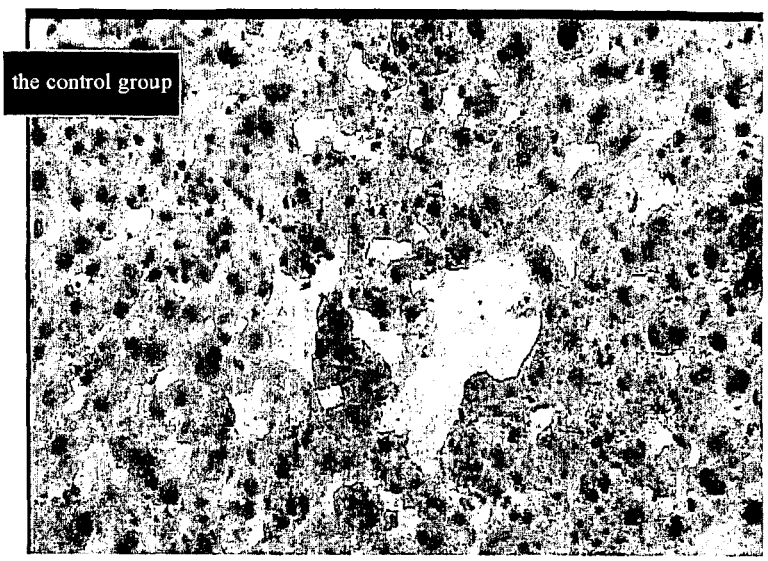
FIG. 1 is the photograph of hepar tissue slice of the mice with hyperlipidemia (normal diet) in the control group after experiment.

The invention is further illustrated by reference to the following examples, which are not intended to limit the scope of the present invention in any way.

Clinical Test Example

The objective of this test was to investigate the blood lipid lowering effect of the present pharmaceutical composition.

Material

Drugs used in the test were the capsules prepared from the following Example 4 (hereinafter referred to as "HeShouWu Capsule", or in short "HSWC").

Method

A parallel, randomized, double-blinded, placebo-controlled clinical study design was adopted, and the healthy subjects with moderately elevated blood lipid were randomly divided into two groups: twenty subjects for the HSWC group and twenty for the placebo group. Inclusion criteria are healthy subjects with moderately elevated cholesterol levels. Exclusion criteria are those with underlying cardiovascular or other diseases or those in the treatment period of the cardiovascular diseases. During 12 weeks of study, subjects were administrated with the HSWC or the corresponding amount of the placebo, wherein the HSWC were the capsules prepared from Example 4 of the present invention, and the dosage is 3 times/day and 3 capsules/time.

Assessment Indexes and Methods:

Total cholesterol of plasma, Low-density lipoprotein (LDL), High-density lipoprotein (HDL), triglyceride (TG) and other relevant markers of cardiovascular risk.

Compliance of vascular system: Measuring elasticity of arteries and calculating the change in volume associated with the change in blood pressure;

Flow mediated dilatation: Using high-resolution ultrasonic apparatus of brachial artery to measure the change of vein in diameter with reactive hyperaemia; and Cutaneous vascular reactivity: Using Laser Doppler Velocimetry with DC iontophoresis to measure cutaneous blood flux.

Results:

The results showed that the HSWC had a positive effect for reducing the cardiovascular risk and the results had statistical significance.

TABLE 1

Effects of the HSWC on blood pressure

| blood pressure | | systolic pressure | | diastolic pressure | |
|---|---|---|---|---|---|
| | | pre-treatment | post-treatment | pre-treatment | post-treatment |
| HSWC | mean | 131.90 | 124.05 | 73.80 | 73.50 |
| | change | | −5.95 | | −0.41 |
| | t-test | | 0.01 | | 0.85 |
| Placebo | mean | 121.85 | 119.45 | 71.85 | 71.40 |
| | change | | −1.97 | | −0.63 |
| | t-test | | 0.20 | | 0.40 |

Pharmaceutical Test Example

The objective of this test was to investigate the therapeutic effect of the present pharmaceutical composition on hyperlipidemia-associated diseases.

Material

Drugs used in the test were the capsules prepared from Example 7.

Method

Male Apo E knocked-out mice (this type of mouse is the animal model of primary hyperlipidemia) at 10 weeks of age, weighing 20 g, were selected and tested for 2 months, half of which were fed with normal diet (fat: 4.3%, cholesterol: 0.02%, the normal diet group) and the other with high-fatty diet (fat: 16.0%, cholesterol: 1.0%, the high-fatty diet group). Either the normal diet group or the high-fatty diet group was divided into the therapeutic group and the control group, ten for each group. The therapeutic group was administered with the HSWC-dissolved drinking water (the concentration of the drug is about 0.8 g/L), so that the dosage of the drug for the normally-drinking mouse is about 90~160 mg drug/kg/d (expressed in the total amount of the crude medicines) for 2 months, and the control group with the HSWC-free drinking water. After experiment, all mice were executed and their liver, kidney and aortic vessel were taken out to make into tissue slice, and stained with oil-red O for the observation by microscope.

Results

Figure 2:
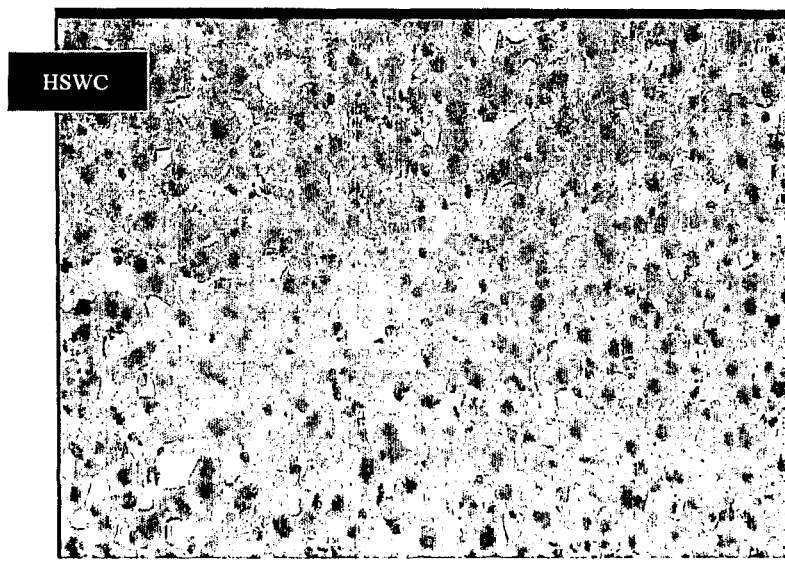
FIG. 2 is the photograph of hepar tissue slice of the mice with hyperlipidemia (normal diet) in the therapeutic group after experiment.
Figure 3:
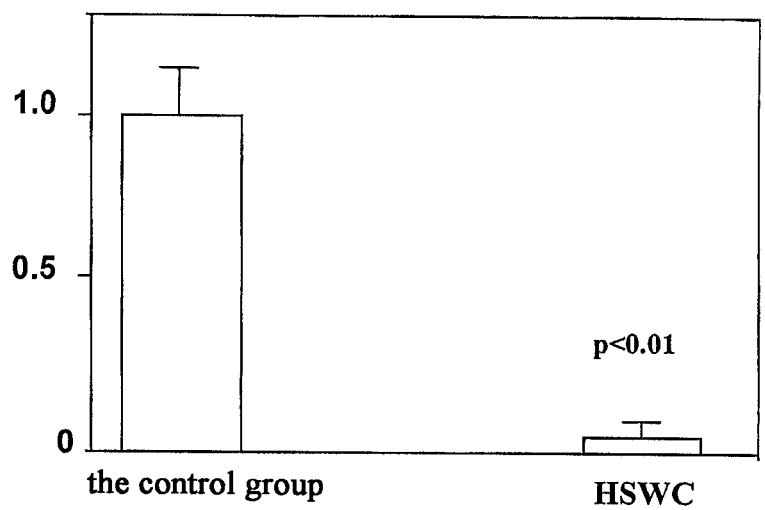
FIG. 3 is the statistical analysis on hepatic steatosis of the mice with hyperlipidemia (normal diet) in the control group and the therapeutic group after experiment.
Figure 4:
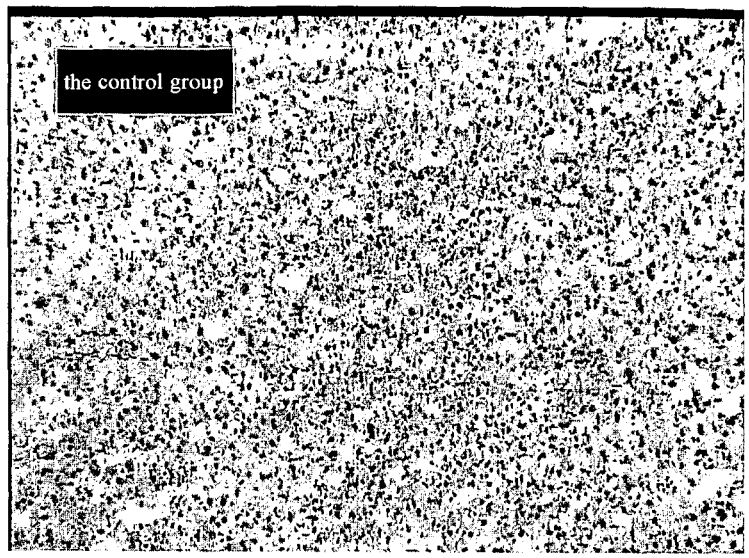
FIG. 4 is the photograph of hepar tissue slice of the mice with hyperlipidemia (high-fatty diet) in the control group after experiment.
Figure 5:
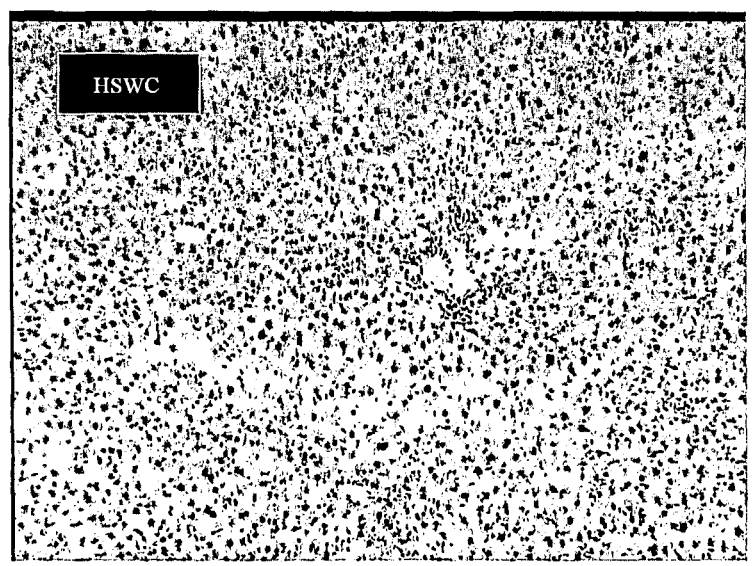
FIG. 5 is the photograph of hepar tissue slice of the mice with hyperlipidemia (high-fatty diet) in the therapeutic group after experiment.
Figure 6:
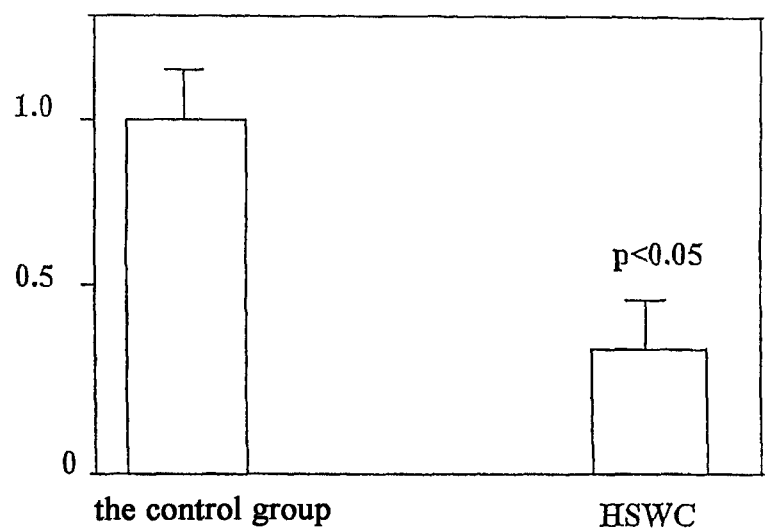
FIG. 6 is the statistical analysis on hepatic steatosis of the mice with hyperlipidemia (high-fatty diet) in the control group and the therapeutic group after experiment.
Figure 7:
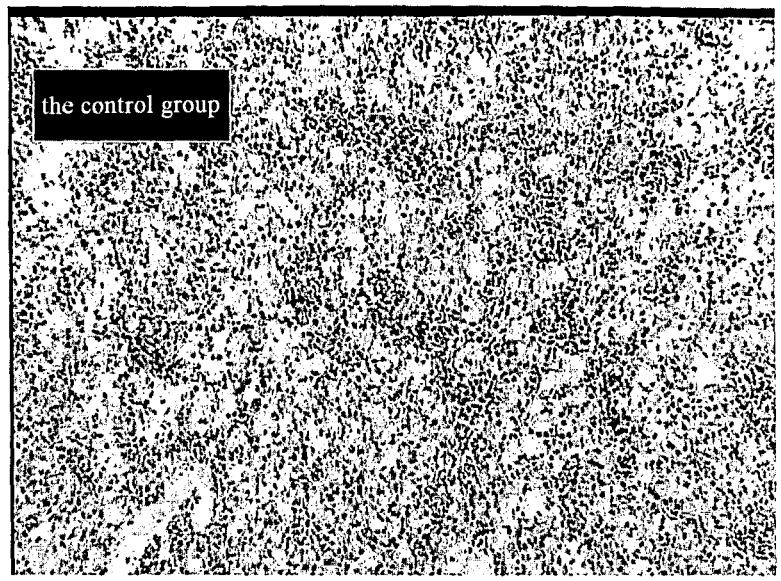
FIG. 7 is the photograph of renal tissue slice of the mice with hyperlipidemia (high-fatty diet) in the control group after experiment.
Figure 8:
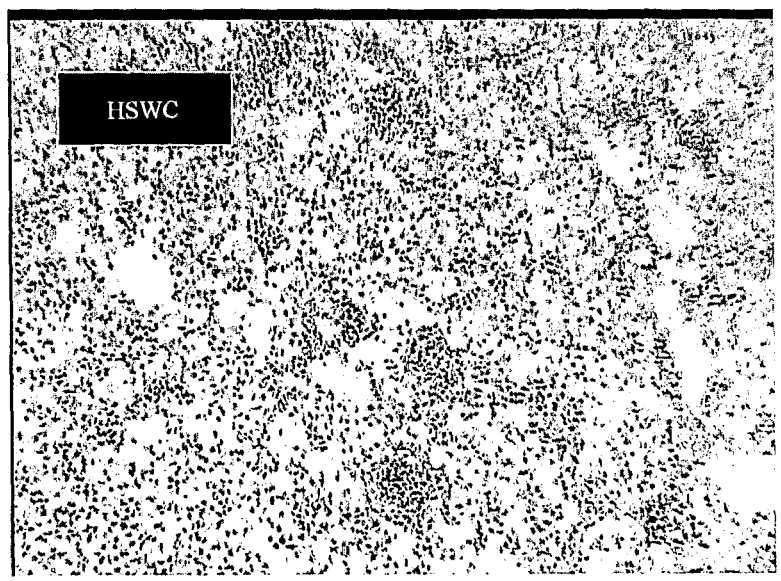
FIG. 8 is the photograph of renal tissue slice of the mice with hyperlipidemia (high-fatty diet) in the therapeutic group after experiment.
Figure 9:
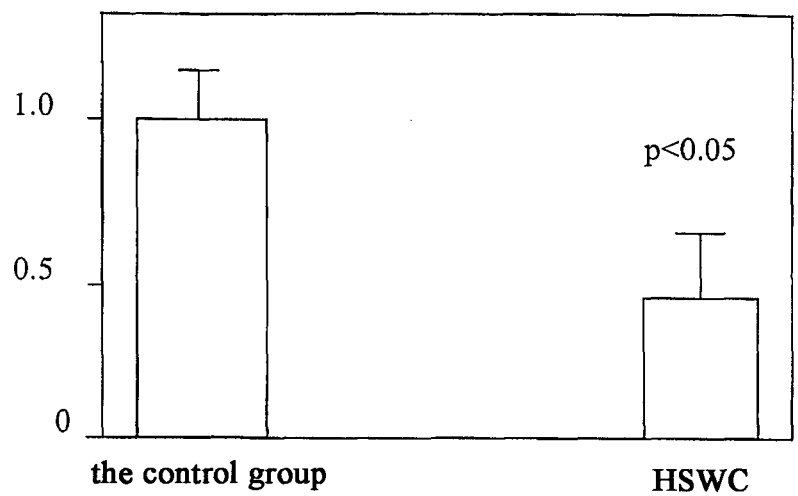
FIG. 9 is the statistical analysis on renal glomerulus lipid deposition of the mice with hyperlipidemia (high-fatty diet) in the control group and the therapeutic group after experiment.
Figure 10:
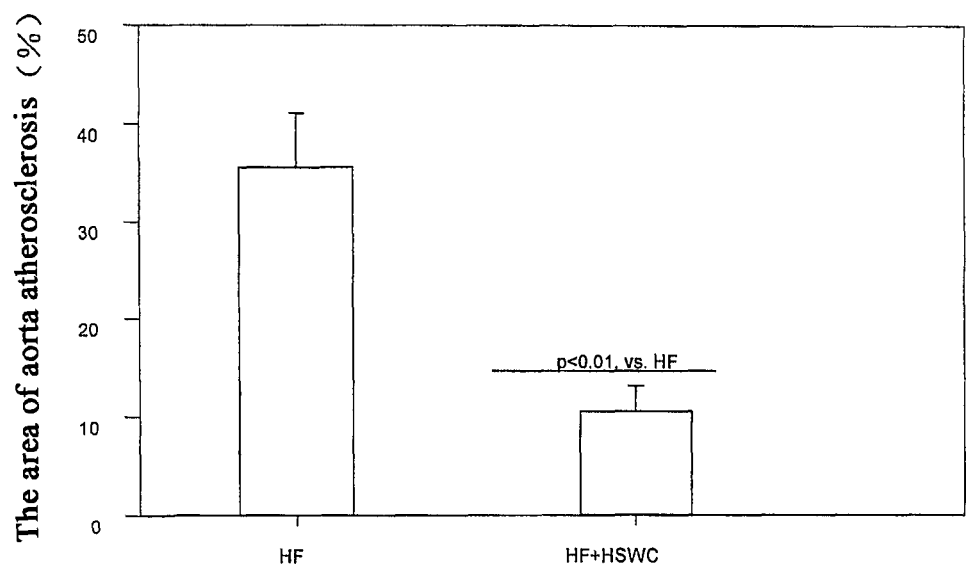
FIG. 10 is the statistical analysis on aorta atherosclerosis of the mice with hyperlipidemia (high-fatty diet) in the control group and the therapeutic group after experiment, wherein said "HF" refers to high-fatty diet.

The results showed that the HSWC could markedly relieve the hepatic steatosis not only in the normal diet group (see FIGS. 1~3), but also in the high-fatty diet group (see FIGS. 4~6). Meanwhile, it could also hamper the development of atherosclerosis of aorta (see FIG. 10) and lipid deposition of renal glomerulus in the high-fatty diet group (see FIGS. 7~9). By statistical analysis, all of aforesaid improvements were considered to be statistically significant.

Preparation Example 1

1. Providing the crude medicines as follows: 150 g of *Polygonum multiflorum* Thunb, 100 g of *Salvia miltiorrhiza* Bunge, 150 g of Fructus Crataegi and 50 g of Radix Notoginseng;
2. Pulverizing above medicinal materials into powder, sifting through 80-mesh sieve and loading into 1500 capsules.

The amount of the crude medicines is 0.3 g in each capsule.

Preparation Example 2

1. Providing the crude medicines as follows: 100 g of *Polygonum multiflorum* Thunb, 60 g of *Salvia miltiorrhiza* Bunge, 100 g of Fructus Crataegi and 10 g of Radix Notoginseng;

TABLE 2

Effects of the HSWC on cholesterol, TG, HDL and LDL in blood

| blood lipid | | cholesterol | | TG | | HDL | | LDL | |
|---|---|---|---|---|---|---|---|---|---|
| | | pre-treatment | post-treatment | pre-treatment | post-treatment | pre-treatment | post-treatment | pre-treatment | post-treatment |
| HSWC | mean | 6.51 | 6.28 | 4.10 | 3.88 | 1.92 | 1.88 | 1.22 | 1.14 |
| | change | | −3.65 | | −5.37 | | −6.40 | | −6.96 |
| | t-test | | 0.09 | | 0.11 | | 0.70 | | 0.23 |
| Placebo | mean | 6.79 | 6.78 | 4.43 | 4.36 | 1.71 | 1.66 | 1.71 | 1.69 |
| | change | | −0.13 | | −1.54 | | −3.30 | | −1.39 |
| | t-test | | 0.95 | | 0.54 | | 0.26 | | 0.77 |

It can be seen from the above results that compared with the placebo group, the HSWC group showed a significant difference.

2. Pulverizing above medicines into powder, sifting through 80-mesh sieve and loading into 900 capsules.

The amount of the crude medicines is 0.3 g in each capsule.

Preparation Example 3

1. Providing the crude medicines as follows: 200 g of *Polygonum multiflorum* Thunb, 130 g of *Salvia miltiorrhiza* Bunge, 200 g of Fructus Crataegi and 100 g of Radix Notoginseng;
2. Pulverizing above medicines into powder, passing through 80-mesh sieve and loading into 2100 capsules.

The amount of the crude medicines is 0.3 g in each capsule.

Preparation Example 4

1. Providing the crude medicines as follows: 150 g of *Polygonum multiflorum* Thunb, 100 g of *Salvia miltiorrhiza* Bunge, 150 g of Fructus Crataegi and 50 g of Radix Notoginseng.
2. The extracts was prepared by a process as follows:

Preparation of *Polygonum multiflorum* Thunb extract: *Polygonum multiflorum* Thunb was weighed and extracted by percolating with 80% ethanol. Resulting extract was applied on a column of macroporous absorptive resin and eluted with 50% ethanol. The elutant was collected, and concentrated by recovering ethanol under reduced pressure and further heated to give 15 g of *Polygonum multiflorum* Thunb extract powder;

Preparation of the extract of *Salvia miltiorrhiza* Bunge and Radix Notoginseng: The coarse powder of the two medicines was placed in an extraction tank, into which water (×5 folds) was added and decocted for 2 hours. After filtration, the residues were further decocted with water (×4 folds) for 1 hour. Filtrating, the residue was discarded. The filtrates were combined and concentrated under reduced pressure to give an extract with a ratio of decoction volume (L) to medicine weight (kg) as 1:1 (V/W). 95% ethanol was added slowly to make the concentration of ethanol at 69~71%. Stand it still for 12 hours. The supernate after alcohol precipitation with was taken out, filtrated and concentrated by recovering ethanol to obtain 15 g of the extract powder of *Salvia miltiorrhiza* Bunge and Radix Notoginseng.

Preparation of Fructus Crataegi extract: Fructus Crataegi was weighed and extracted with 50% ethanol (×15 folds) twice, 60 minutes for each time. Resulting extracts were combined and concentrated by recovering ethanol, and further concentrated to give 15 g of the Fructus Crataegi extract powder.

3. Mixing well aforesaid extracts of Step 2, into which 0.45 g of talc powder and 2.7 g of dextrine were added, and the mixture was loaded into 150 capsules.

The amount of the aforesaid extracts is 0.3 g in each capsule, which corresponds to 3 g of the crude medicines.

Preparation Example 5

The capsules were prepared according to the process of Example 4, except that 0.9 g of talc powder and 3.15 g of dextrine were added, and the mixture was loaded into 150 capsules.

The amount of the aforesaid extracts is 0.3 g in each capsule, which corresponds to 3 g of the crude medicines.

Preparation Example 6

1. Providing the crude medicines as follows: 100 g of *Polygonum multiflorum* Thunb, 60 g of *Salvia miltiorrhiza* Bunge, 100 g of Fructus Crataegi and 10 g of Radix Notoginseng;
2. The *Polygonum multiflorum* Thunb extract and the Fructus Crataegi extract were prepared by the process of Example 4, and 10 g of the *Polygonum multiflorum* Thunb extract powder and 10 g of the Fructus Crataegi extract powder were obtained;
3. The *Salvia miltiorrhiza* Bunge extract and the Radix Notoginseng extract were prepared by a process as follows:

Preparation of the *Salvia miltiorrhiza* Bunge extract: the medicinal material of *Salvia miltiorrhiza* Bunge was pulverized and passed through 20-mesh sieve and extracted with water by heating twice: for the first time, the medicinal material was soaked in water (×9~10 folds) and extracted by heating for 1.5 hours, and for the second time, water (×5~7 folds) was added and extracted by heating for 1 hour. Resulting decoctions were combined, concentrated properly and 95% ethanol was added to make the concentration of ethanol at 50~70%, concentrated by recovering ethanol to give 6 g of the *Salvia miltiorrhiza* Bunge extract powder.

Preparation of the Radix Notoginseng extract: the medicinal material of Radix Notoginseng was taken and extracted with 10%~30% ethanol (×10 folds) for three times, refluxing by heating 8 hours. Resulting extracts were combined, concentrated by recovering ethanol to give 1 g of the Radix Notoginseng extract powder.

4. Mixing well the extracts of Step 2 and Step 3, into which 0.27 g of talc powder and 1.62 g of dextrine were added, and the mixture was loaded into 90 capsules.

The amount of the aforesaid extracts is 0.3 g in each capsule, which corresponds to 3 g of the crude medicines.

Preparation Example 7

The capsules were prepared according to the process of Example 4, except that 0.72 g of talc powder and 2.86 g of dextrine were added, and the mixture was loaded into 150 capsules.

The amount of the aforesaid extracts is 0.3 g in each capsule, which corresponds to 3 g of the crude medicines.

Preparation Example 8

1. Providing the crude medicines as follows: 200 g of *Polygonum multiflorum* Thunb, 130 g of *Salvia miltiorrhiza* Bunge, 200 g of Fructus Crataegi and 100 g of Radix Notoginseng.
2. 20 g of the *Polygonum multiflorum* Thunb extract powder, 20 g of the Fructus Crataegi extract powder, 13 g of the *Salvia miltiorrhiza* Bunge extract powder and 10 g of the Radix Notoginseng extract powder were prepared by the process of Example 6;
3. Mixing well the extracts of Step 2, into which 1.01 g of talc powder and 4.02 g of dextrine were added, and the mixture was loaded into 210 capsules.

The amount of the aforesaid extracts is 0.3 g in each capsule, which corresponds to 3 g of the crude medicines.

Preparation Example 9

1. Providing the crude medicines as follows: 200 g of *Polygonum multiflorum* Thunb, 130 g of *Salvia miltiorrhiza* Bunge, 200 g of Fructus Crataegi and 100 g of Radix Notoginseng.
2. 20 g of the *Polygonum multiflorum* Thunb extract powder, 20 g of the Fructus Crataegi extract powder, 13 g of the *Salvia miltiorrhiza* Bunge extract powder and 10 g of the Radix Notoginseng extract powder were prepared by the process of Example 6;

3. Adding a suitable amount of lactose into the above extracts, and was prepared into 210 tablets.

The amount of the aforesaid extracts is 0.3 g in each tablet, which corresponds to 3 g of the crude medicines.

The preceding description has disclosed the embodiments of the present invention. It is to be understood for the skilled in the art that various variations and modification can be made without departing from the essential spirit of the present invention, which are encompassed within the scope of the present invention.

What is claimed is:

1. A pharmaceutical composition with blood lipid lowering effect, consisting of:
    *Polygonum multiflorum* Thunb extract, *Salvia miltiorrhiza* Bunge extract, Fructus Crataegi extract, Radix Notoginseng extract and optionally, a pharmaceutically acceptable carrier;
    wherein the composition is prepared by a process comprising pulverizing herbs consisting of 10 to 20 parts of *Polygonum multiflorum* Thunb, 5 to 15 parts of *Salvia miltiorrhiza* Bunge, 10 to 20 parts of Fructus Crataegi and 1 to 10 parts of Radix Notoginseng, extracting each herb
    and combining all of the extracts;
    wherein the *Polygonum multiflorum* Thunb extract is prepared by a process selected from water extraction or alcohol extraction followed by separation with macro-porous resin;
    wherein the *Salvia miltiorrhiza* Bunge extract is prepared by a process selected from water extraction, alcohol extraction, water extraction with alcohol precipitation or by water extraction with alcohol precipitation followed by separation with macro-porous resin;
    wherein the Fructus Crataegi extract is prepared by a process selected from water extraction, water extraction followed by separation with polyamide resin or ethanol extraction; and
    wherein the Radix Notoginseng extract is prepared by a process selected from ethanol extraction, water extraction with alcohol precipitation or alcohol extraction followed by separation with macro-porous resin.

2. The pharmaceutical composition according to claim 1, wherein the composition contains the pharmaceutically acceptable carrier.

3. The pharmaceutical composition according to claim 2, wherein the pharmaceutically acceptable carrier is selected from the group consisting of starch, lactose, talc powder, dextrine and combinations thereof.

4. The pharmaceutical composition according to claim 1, wherein the composition is an oral preparation.

5. The pharmaceutical composition according to claim 4, wherein the composition is a tablet, granule or capsule.

6. The pharmaceutical composition of according to claim 1, wherein after extracting each herb and prior to combining all of the extracts, each extract is prepared into a powder.

7. The pharmaceutical composition according to claim 1, wherein after pulverizing each of the herbs, each of the herbs are dried at a temperature of about 50-60° C.

8. The pharmaceutical composition according to claim 1, wherein said pulverizing comprises pulverizing herbs consisting of:
    15 parts of *Polygonum multiflorum* Thunb,
    10 parts of *Salvia miltiorrhiza* Bunge,
    15 parts lay of Fructus Crataegi and
    5 parts of Radix Notoginseng.

9. A method for preparing a pharmaceutical composition comprising:
    pulverizing herbs consisting of 10 to 20 parts of *Polygonum multiflorum* Thunb, 5 to 15 parts of *Salvia miltiorrhiza* Bunge, 10 to 20 parts of Fructus Crataegi and 1 to 10 parts of Radix Notoginseng, extracting each herb, combining all of the extracts and optionally adding a pharmaceutically acceptable carrier;
    wherein extracting comprises:
    extracting the *Polygonum multiflorum* Thunb by a process selected from water extraction or alcohol extraction followed by separation with macro-porous resin;
    extracting *Salvia miltiorrhiza* Bunge by a process selected from water extraction, alcohol extraction, water extraction with alcohol precipitation or by water extraction with alcohol precipitation followed by separation with macro-porous resin;
    extracting Fructus Crataegi by a process selected from water extraction, water extraction followed by separation with polyamide resin or ethanol extraction; and
    extracting Radix Notoginseng extract by a process selected from ethanol extraction, water extraction with alcohol precipitation or alcohol extraction followed by separation with macro-porous resin.

10. The method according to claim 9, wherein said pharmaceutically acceptable carrier is added and wherein the pharmaceutically acceptable carrier is selected from the group consisting of starch, lactose, talc powder, dextrin and combinations thereof.

11. The method according to claim 9, further comprising, after pulverizing the herbs, drying the pulverized herbs at a temperature of about 50-60° C.

12. The method according to claim 9, further comprising preparing an oral preparation of the combined extracts.

13. The method according to claim 9, wherein oral preparations include tablets, granules or capsules.

14. The method according to claim 9, wherein the administration of the pharmaceutical composition occurs once, twice or three times per day.

15. A method for reducing blood lipid level, comprising: orally administering to a patient in need thereof, a therapeutically effective amount of the pharmaceutical composition of claim 1.

16. A method for the treatment and/or prevention of hyperlipidemia, comprising: orally administering to patient in need thereof, a therapeutically effective amount of the pharmaceutical composition of claim 1.

17. A method for the treatment and/or prevention of fatty liver, comprising: orally administering to patient in need thereof, a therapeutically effective amount of the pharmaceutical composition of claim 1.

18. The method for reducing blood lipid level, according to claim 15, wherein said blood lipid is cholesterol.

19. The method according to any one of claims 15, 16 or 17, wherein the method comprises administration of 10-50 g of the pharmaceutical composition.

20. The method according to claim 19, wherein the method comprises administration of 20-30 g of the pharmaceutical composition.

21. The method according to claim 20 wherein the administration of the pharmaceutical composition occurs once, twice or three times per day.

22. The method according to claim 19, wherein the administration of the pharmaceutical composition occurs once, twice or three times per day.

* * * * *